United States Patent [19]

Cushman et al.

[11] Patent Number: 4,983,176
[45] Date of Patent: Jan. 8, 1991

[54] DEFORMABLE PLASTIC SURGICAL CLIP

[75] Inventors: Robert Cushman, Cedar Crest; Wolff M. Kirsch; Yong H. Zhu, both of Albuquerque, all of N. Mex.

[73] Assignee: University of New Mexico, Albuquerque, N. Mex.

[21] Appl. No.: 319,297

[22] Filed: Mar. 6, 1989

[51] Int. Cl.$^5$ .............................................. A61B 17/00
[52] U.S. Cl. .................................... 606/151; 606/142; 606/216
[58] Field of Search ............... 128/325, 337, 346, 335; 606/139, 142, 157, 158, 151

[56] References Cited

U.S. PATENT DOCUMENTS

| | | | |
|---|---|---|---|
| 4,217,902 | 8/1980 | March | 128/325 |
| 4,637,395 | 1/1987 | Caspar et al. | 128/334 R |
| 4,741,337 | 5/1988 | Smith et al. | 128/334 R |
| 4,796,627 | 1/1989 | Tucker | 128/337 |
| 4,821,721 | 4/1989 | Chin et al. | 128/334 R |
| 4,832,027 | 5/1989 | Utz | 128/337 |

Primary Examiner—Randall L. Green
Assistant Examiner—Gary Jackson
Attorney, Agent, or Firm—Hoffman, Wasson & Gitler

[57] ABSTRACT

A plastic surgical clip comprises a pair of arms having inturned opposing tips, the arms being joined by a bridge having a lesser cross-section to provide a locus for bending by drawing the ears in parallel directions against an intermediate support.

2 Claims, 1 Drawing Sheet

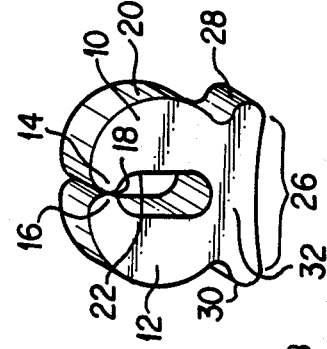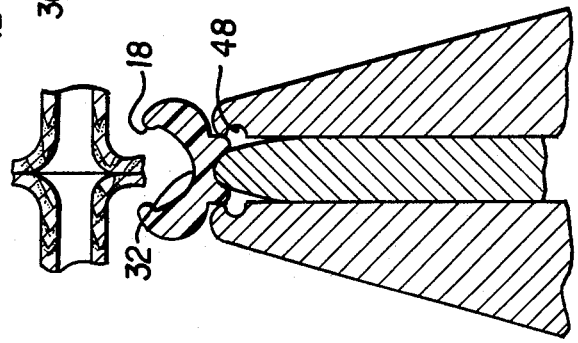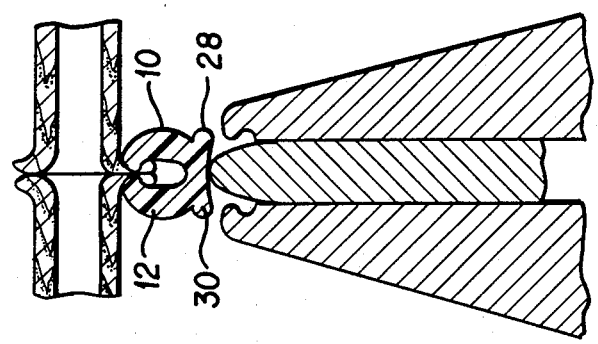

DEFORMABLE PLASTIC SURGICAL CLIP

BACKGROUND

This invention relates to the field of surgery, and more particularly to a plastic clip and method of applying the clip to tissues, particularly in microsurgical anastomoses.

The term "anastomosis" covers a variety of procedures in which blood vessels or other tubular members, such as parts of the colon, are joined or reconnected. Vessels may be joined in a variety of relative orientations, including end-to-side, and end-to-end. Solid tubular structures such as peripheral nerves can also be joined together, as well as solid structures such as subcutaneous tissue and skin.

Anastomoses are traditionally performed by suturing the vessels together at the juncture between them. Alternatives to suturing have been developed, in order to prevent thrombosis which tends to occur at the points of penetration of the sutures. One such alternative, particularly for larger vessels, involves mechanical connectors such as collars. A second alternative is the use of surgical clips which are applied along the vessel juncture to perform a holding function similar to that of sutures, without penetrating the vessel walls. Two such clips, developed by the present inventors, are shown in U.S. Pat. Nos. 4,586,503 and 4,733,660. As described in the former patent, the clips are applied over apposed edges of the vessels, the edges first being everted (turned outward) to form flanges that are gripped between the jaws of the clips.

The clips disclosed in the above patents are preferably made of metal, and are crimped (plastically deformed) in place over the edges of the everted tissues. This invention is distinguished from the above-mentioned patents in that the clips now proposed are made of plastic, which has certain advantages noted below, and in that rather than being crimped, the clips are opened by temporarily spreading their jaws, then allowed to recover to their original shape around the apposed tissues.

Plastic materials have a "memory" which causes them to return to their original shape in time, following deformation. This characteristic is used to advantage in the present invention. Furthermore, the use of plastic can be advantageous in that there are bioabsorbable plastics which may be employed at internal sites where bioabsorption is preferred or necessary for proper healing.

SUMMARY OF THE INVENTION

In view of the foregoing, it is an object of the invention to provide a surgical clip made of plastic, with structure which facilitates application by a simple tool.

Another object is to provide a bioabsorbable surgical clip.

These and other objects are met by a surgical clip comprising a unitary body made of plastic, the body including a pair of arms, having opposed inturned tips, a bridge interconnecting the arms, a pair of ears extending in opposite directions from the bridge, the bridge having a substantially flat outer edge, whereby the ears may be pulled by a tool while a center portion of the bridge is supported, to generate a force couple for opening the arms for placement over apposed tissue edges.

The invention is also directed to a method of applying a surgical clip having holding ears thereon, comprising steps of holding the clip by its ears with a tool, supporting the clip at a point midway between its ears, pulling back on the ears to open the clip, placing the ears over the tissue edges, and releasing the ears from the tool, thereby allowing the clip to spring back in position over the tissues.

BRIEF DESCRIPTION OF THE DRAWINGS

In the accompanying drawings,

FIG. 1 is a perspective view of a surgical clip embodying the invention;

FIG. 2 is a sectional view thereof, shown mounted in an applying tool ready for use;

FIG. 3 is a view corresponding to FIG. 2, showing the clip, in its temporarily opened position, being placed over the apposed everted edges of a vessel; and FIG. 4 shows the clip, released from the tool, securing the tissues together.

DESCRIPTION OF THE PREFERRED EMBODIMENT

As shown in FIG. 1, a surgical clip embodying the invention includes a unitary piece formed from a biologically absorbable plastic. Those in the field of surgery can identify suitable plastics for various applications.

The clip comprises a pair of arms 10,12 having inturned tips 14,16 with gripping edges 18 which are slightly rounded to avoid puncturing or tearing the tissues over which they are applied. The radius of curvature should be at least 0.0001 inch for a clip 0.01 inch in height.

The arms have rounded outer edges 20, and inner edges 22 which are linear for most of their length. The resultant thickening stiffens the arms against bending at their midpoints, and creates a preferred zone Z for flexure.

The arms are interconnected by a bridge 26 which in its relaxed state is essentially linear, extending past its junctions with the arms to opposed "ears" 28,30. It will be seen that the width of the clip is substantially greater at the midpoint of the arms than in the vicinity of the bridge. It follows that the bridge portion of the clip is, compared to the arm portions, relatively easily deformed or bent when subjected to bending forces. This characteristic is clearly illustrated in FIG. 3, where a bending moment is applied to the bridge by pulling downward on the ears while supporting the bridge at its center 32.

A portion of a tool for opening and manipulating the clip is illustrated in FIGS. 2-4. The tool comprises a pair of jaws 40,42 fixed with respect to one another, and a center support or anvil 44 having a rounded, tapered tip 46. Each jaw has a groove 48 near its tip 50, for holding the clip by its ears, as shown in FIG. 2. The tool includes means (not shown) for causing relative displacement between the jaws and the anvil in response to certain manipulation of the tool by the surgeon, for example by squeezing a pair of handles. Various suitable tool constructions will readily occur to those of skill in the art.

In operation, with the anvil in the retracted position of FIG. 2, a clip is inserted laterally between the jaws of the tool, so that the ears rest within and are held by the grooves 48. The tool now is useable as a manipulator, to move the clip into position for application to apposed tissues, for example everted vessel ends as shown in FIG. 3.

Once the clip is in proper position, the anvil of the tool is advanced, applying a force to the center of the bridge of the clip that is resisted by reaction forces between the clip ears and the grooves. The resulting force couples create a bending moment in the bridge which is greatest nearest its center; the bending deformation is particularly great near the center of the bridge, as shown in FIG. 3. The clip material, chosen for its ability to withstand substantial strain, allows the bridge to bend sufficiently that as the bridge bends further around the tip of the anvil, the ears escape from the grooves. At this point, the clip tends to spring forward toward the tissues, which helps produce firm engagement of the clip. The speed of springback depends on the hysteresis characteristics of the plastic material chosen, but in any event, the clip soon returns to its original configuration, now binding the tissues together without penetrating them. As healing occurs, the clips may be removed, or absorbed, depending upon their placement and material.

Inasmuch as the embodiment described above, and shown in the accompanying drawings, is subject to variations and modifications, it is intended that the foregoing shall be interpreted only as illustrative of the invention defined by the following claims.

I claim:

1. A method of joining tissue edges with a surgical clip having holding ears thereon, comprising steps of holding said clip by its ears with a tool,
supporting said clip against rearward movement at a point midway between its ears, while
pulling back on said ears to open said clip,
placing said arms over said tissue edges, and then
releasing said ears from said tool, thereby allowing the clip to spring back in position over said tissues.

2. A surgical clipping system, comprising a surgical clip comprising
a unitary body made of plastic, said body including
a pair of arms having opposed inturned tips,
a bridge interconnecting said arms, the arms extending in a forward direction from opposite edges of the bridge, and
a pair of ears extending in opposite directions from the ends of said bridge, said bridge having a substantially flat rearward edge, in combination with
a tool having a pair of spaced jaws with opposed grooves therein for engaging said clip ears, and an anvil between said jaws and relatively movable with respect thereto, for applying bending forces to said bridge between said ears so as to open said clip,
said grooves and ears being complementary and configured to allow said clip to escape from said grooves after a predetermined amount of bending of said bridge.

* * * * *